United States Patent
Nixon

(10) Patent No.: US 8,360,577 B2
(45) Date of Patent: Jan. 29, 2013

(54) SYSTEM, METHOD, AND COMPUTER SOFTWARE CODE FOR GRADING A CATARACT

(75) Inventor: Donald Ray Nixon, Barrie (CA)

(73) Assignee: Oculus Optikgerate GmbH, Wetzler (DE)

( * ) Notice: Subject to any disclaimer, the term of this patent is extended or adjusted under 35 U.S.C. 154(b) by 347 days.

(21) Appl. No.: 12/614,689

(22) Filed: Nov. 9, 2009

(65) Prior Publication Data

US 2010/0118266 A1    May 13, 2010

Related U.S. Application Data

(60) Provisional application No. 61/193,230, filed on Nov. 7, 2008.

(51) Int. Cl.
*A61B 3/14* (2006.01)
*A61B 3/10* (2006.01)
*A61B 3/00* (2006.01)

(52) U.S. Cl. .......................... 351/206; 351/221; 351/246

(58) Field of Classification Search .................. 351/206, 351/221, 246; 604/22; 606/4, 6, 107
See application file for complete search history.

(56) References Cited

U.S. PATENT DOCUMENTS

| 2002/0052551 | A1 | 5/2002 | Sinclair et al. | |
| 2004/0106929 | A1* | 6/2004 | Masket | 606/107 |
| 2011/0091084 | A1* | 4/2011 | Li et al. | 382/128 |

FOREIGN PATENT DOCUMENTS

CA    2596560    2/2009

OTHER PUBLICATIONS

Masters, B.R., "Three-Dimensional Microscopic Tomographic Imaging of the Cataract in a Human Lens in Vivo," Optics Express, Oct. 26, 1998, pp. 332-338, vol. 3, No. 9.
Nixon, Donald R., unpublished drawings in CA 2,596,560, Feb. 20, 2009.

* cited by examiner

*Primary Examiner* — Ricky Mack
*Assistant Examiner* — Mahidere Sahle
(74) *Attorney, Agent, or Firm* — Terry M. Sanks, Esq.; Beusse Wolter Sanks Mora & Maire, P.A.

(57) ABSTRACT

A method for grading a cataract, the method including creating a three-dimensional image of at least most of a lens of an eye having a cataract from information received from an imaging system, comparing the three-dimensional image with a first template to determine an optical density of the lens, and determining a grade for the cataract based on the comparison of the optical density of the lens and a volume of the first template. A system and computer software code for grading a cataract are also disclosed.

19 Claims, 3 Drawing Sheets

| LOCS III | CGS |
|---|---|
| Grade 1 | Vol. 20.79 mm³, mean optical density ≤ 13% |
| Grade 2 | Vol. 20.79 mm³, mean optical density 14-16% |
| Grade 3 | Vol. 20.79 mm³, mean optical density 17-19% |
| Grade 4 | Vol. 20.79 mm³, mean optical density ≥ 20%<br>Vol. 30.97 mm³, mean optical density < 20% |
| Grade 5 | Vol. 20.79 mm³, mean optical density ≥ 20%<br>Vol. 30.97 mm³, mean optical density ≥ 20% |

US 8,360,577 B2

SYSTEM, METHOD, AND COMPUTER SOFTWARE CODE FOR GRADING A CATARACT

CROSS-REFERENCE TO RELATED APPLICATIONS

This application claims the benefit of U.S. Provisional Application No. 61/193,230 filed Nov. 7, 2008, and incorporated herein by reference in its entirety.

BACKGROUND OF THE INVENTION

Embodiments of the invention relate to cataract surgery, and more specifically, to objectively grading a cataract.

A cataract is a clouding that develops in the crystalline lens of the eye (or pupil) or in its envelope, varying in degree from slight to complete opacity and obstructing the passage of light. Surgical procedures may be used to remove cataracts. Grading of a cataract is performed prior to removal though. The importance of pre-operative grading allows for the pre-programming of cataract surgical equipment to ideally match a grade of the cataract to an appropriate energy setting and fluid setting to most efficiently remove the cataract.

Cataracts may be graded by visual inspection and assignment of numerical values to indicate severity. Grading systems currently known to evaluate a cataract are the Oxford Clinical Cataract Classification and Grading System, the Johns Hopkins system, and the Lens Opacity Classification System (LOCS, LOCS II, and LOCS III). In general, photographs of slit lamp cross-sections of the lens are used as references for grading nuclear opalescence and nuclear color, and photographs of the lens seen by retroillumination are used as references for grading cortical and posterior subcapsular cataract. More specifically, with respect to the LOCS III, cataracts are examined based on individual components, such as nuclear, cortical, and posterior sub capsular, in comparison to a series of photographic graded images printed on paper. A subjective comparison is then made between a patient's cataract to the photographic series to determine where the individual cataract would match against the photographic series so as to establish a graded number. Thus, the comparison is performed based on an examiner's perspective rather than a perspective that is replicable examiner to examiner.

Existing grading system relies on subjectivity, which the inventor believes is too subjective, with respect to grading cataracts. Because of the subjectivity which allows for varied interpretation, difficulties arise in comparing a particular density of a cataract and equating it to different surgical techniques and parameters in order to remove it.

Surgeons and surgical equipment manufacturers, such as but not limited to phacomulsification ("phaco") technology manufacturers, and those with cataracts would benefit from a system and method that provided an objective grading of a cataract wherein the system and method are also reproducible for use at any location where cataracts are graded. Furthermore, such a reproducible system and method would be beneficial to allow for a better comparison between surgeons and surgical equipment manufacturers as to what generates the least amount of energy and fluid consumption inside the eye when comparing different cataract grades.

BRIEF DESCRIPTION OF THE INVENTION

Embodiments of the present invention relate a system, method, and computer software code for objectively grading a cataract wherein the grading of any cataract may be replicated regardless of an examiner and/or a location where the grading is performed.

The method comprises creating a three-dimensional image of at least most of a lens of an eye having a cataract from information received from an imaging system. The method further comprises comparing the three-dimensional image with a first template to determine an optical density of the lens. The method also comprises determining a grade for the cataract based on the comparison of the optical density of the lens and a volume of the first template.

The system comprises an imaging system that captures a three-dimensional image of at least most of a lens of an eye having a cataract. The system also comprises a first template having a defined volume. The system further comprises a processor that compares the three-dimensional image with a first template to determine an optical density of the lens, and determines a grade for the cataract based on the comparison of the optical density of the lens and a volume of the first template.

The computer software code comprises a computer software module for creating a three-dimensional image of at least most of a lens of an eye having a cataract from information received from an imaging system. The computer software code also comprises a computer software module for comparing the three-dimensional image with a first template to determine an optical density of the lens. The computer software code also comprises a computer software module for determining a grade for the cataract based on the comparison of the optical density of the lens and a volume of the first template. The computer software code is stored on a computer readable medium, and is configured for execution with a processor for grading a cataract.

BRIEF DESCRIPTION OF THE DRAWINGS

A more particular description of the invention briefly described above will be rendered by reference to specific embodiments thereof that are illustrated in the appended drawings. Understanding that these drawings depict only typical embodiments of the invention and are not therefore to be considered to be limiting of its scope, exemplary embodiments of the invention will be described and explained with additional specificity and detail through the use of the accompanying drawings in which.

DETAILED DESCRIPTION OF THE INVENTION

Figure 1:
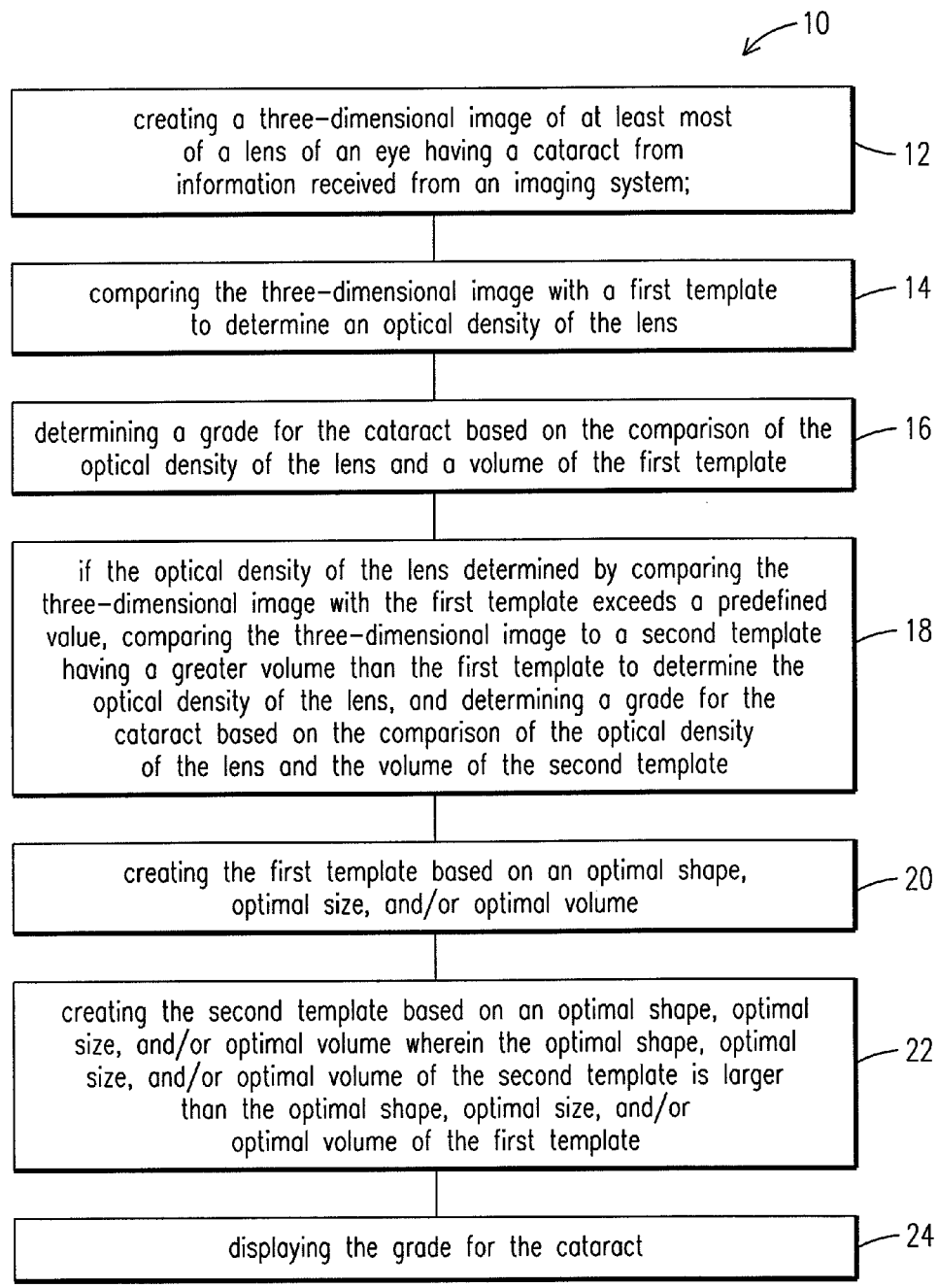
FIG. 1 is a flowchart illustrating an exemplary embodiment of a method for grading a cataract.

Exemplary embodiments of the invention solve problems in the art by providing a method and system, which may utilize a processor that uses computer implemented method, such as a computer software code or computer readable media, for remotely grading a cataract. Persons skilled in the art will recognize that an apparatus, such as a data processing system, including a CPU, memory, I/O, program storage, a connecting bus, and other appropriate components, could be programmed or otherwise designed to facilitate the practice of the method of the invention. Such a system would include appropriate program means for executing the method of the invention.

Also, an article of manufacture, such as a pre-recorded disk, computer readable media, or other similar computer program product, for use with a data processing system, could include a storage medium and program means recorded thereon for directing the data processing system to facilitate the practice of the method of the invention. Such apparatus and articles of manufacture also fall within the spirit and scope of the invention.

Broadly speaking, a technical effect is to grade a cataract where the grading is uniform to an extent that a grader's subjectivity is not a facture when determining the grade. To facilitate an understanding of the exemplary embodiments of the invention, it is described hereinafter with reference to specific implementations thereof. Exemplary embodiments of the invention may be described in the general context of computer-executable instructions, such as program modules, being executed by any device, such as but not limited to a computer, designed to accept data, perform prescribed mathematical and/or logical operations usually at high speed, where results of such operations may or may not be displayed. Generally, program modules include routines, programs, objects, components, data structures, etc. that perform particular tasks or implement particular abstract data types. For example, the software programs that underlie exemplary embodiments of the invention can be coded in different programming languages, for use with different devices, or platforms. In the description that follows, examples of the invention may be described in the context of a web portal that employs a web browser. It will be appreciated, however, that the principles that underlie exemplary embodiments of the invention can be implemented with other types of computer software technologies as well.

Moreover, those skilled in the art will appreciate that exemplary embodiments of the invention may be practiced with other computer system configurations, including hand-held devices, multiprocessor systems, microprocessor-based or programmable consumer electronics, minicomputers, mainframe computers, and the like. Exemplary embodiments of the invention may also be practiced in distributed computing environments where tasks are performed by remote processing devices that are linked through at least one communications network. In a distributed computing environment, program modules may be located in both local and remote computer storage media including memory storage devices.

Referring now to the drawings, embodiments of the present invention will be described. Exemplary embodiments of the invention can be implemented in numerous ways, including as a system (including a computer processing system), and a method (including a computerized method), an apparatus, a computer readable medium, a computer program product, or a data structure tangibly fixed in a computer readable memory. Several embodiments of the invention are discussed below.

FIG. 1 discloses a flowchart for grading a cataract. After an initial evaluation of the patient and subsequent dilation of at least one pupil, once dilated, the patient is positioned in front of an imaging system 35, or camera, that uses the Scheimpflug principle. Imaging using the Scheimpflug principle differs from conventional technique in that the object plane, lens plane, and image lane are not parallel to each other, but intersect in a common straight line. The major advantage of the Scheimpflug geometry is that a wide depth of focus is achieved. The Scheimpflug principle has been applied in ophthalmology to obtain optical sections of the entire anterior segment of the eye, from the anterior surface of the cornea to the posterior surface of the lens. This type of imaging allows assessment of anterior and posterior corneal topography, anterior chamber depth, as well as anterior and posterior topography of the lens.

An example of an imaging system 5 employing the Scheimpflug principle is the Pentacam™ imaging system manufactured by Oculus of Heidelberg, Germany. The Pentacam™ imaging system comprises a rotating Scheimpflug camera which captures Scheimpflug images of the anterior eye segment, both front and posterior surfaces. The Scheimpflug principle provides sharp and crisp images that include information from the anterior corneal surface to the posterior crystalline capsule. The key advantages of the rotating imaging process are the precise measurement of the central cornea, the correction of eye movements, the easy fixation for the patients and the extremely short examination time. By evaluating reflective light through the Scheimpflug camera, an assessment of the optical density is possible.

A three-dimensional image of at least most of the lens of the eye, or pupil, may be created from information received from the imaging system, at 12. Even though "lens" is used herein, those skilled in the art will readily recognize that lens includes at least most of the lens of the eye or pupil. Limitations that are encountered when creating the three-dimensional image of the lens include the size of the pupil and the penetrating ability of the light source of the camera. Other limitations that may be encountered may involve a density of the cataract and/or a maximum amount of pupilary dilation that could be achieved with pharmaceutical dilating drops.

An optical density, specifically a mean optical density, of at least most of a lens, is determined from comparing the three-dimensional image with a first template, at 14. The term "optical density" describes the opacity of a medium (such as crystalline lens of an eye). The optical density is determined by measuring an amount of back-scattered light. A clear optical medium does not scatter light that passes through it. However, an opaque medium scatters light back to a measuring device. Measuring the back scattered light, and dividing its measurement by a known volume provides for the optical density.

Figures 2, 3:
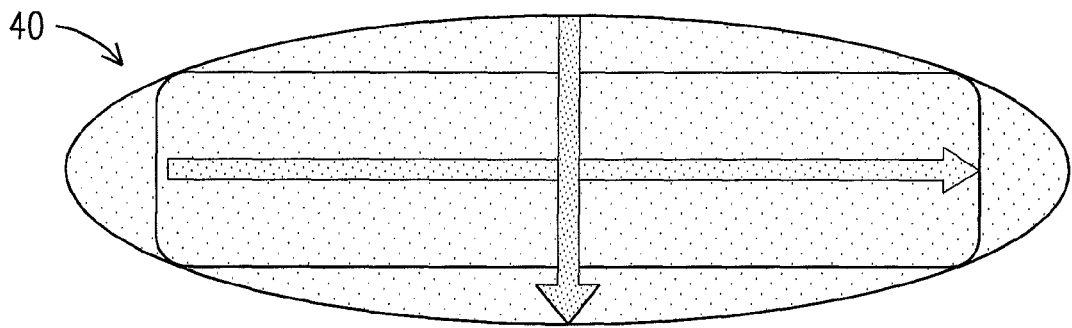
FIG. 2 is an illustration of an exemplary embodiment of a first template.
FIG. 3 is a table illustrating an exemplary embodiment of grade levels compared to LOCS III grade levels.

The first template, Template 1, has a defined volume. The first template 40 is a three-dimensional hybrid between a sphere and a cube. FIG. 2 is an illustration of an exemplary embodiment of the first template 40. The specific shape and volume of the first template 40 is provided to maximize an amount of volume that could be sampled into a human lens while minimizing a percentage of patients that could not be tested through a dilated pupil pre-operatively. The first template 40 has an average diameter of 3.0 millimeters (herein after "mm") to 5.0 mm with a preferred measurement being 4.0 mm, an average depth (or vertical height) of 1.0 mm to 3.0 mm with a preferred measurement being 2.0 mm, an average anterior radius of curvature, r', between 4.0 mm and 6.0 mm with a preferred measurement being 5.0 mm, and an average posterior radius of curvature, r", between 3.0 mm and 5.0 mm with a preferred measurement being 4.0 mm. An average volume of the first template is from 20.0 mm$^3$ to 21.5 mm$^3$ with a preferred measurement being 20.79 mm$^3$.

The first template 40 is created to have an optimal shape, optimal size, and optimal volume that could be used in 3-dimensional reconstruction of the human lens, at 20. A grade for the cataract is determined based on the comparison of the optical density of the lens and the volume of the first template, at 16. The cataract grade may be displayed, at 24.

Because LOCS III already uses a 6 part grade system, Grade 0, Grade 1, Grade 2, Grade 3, Grade 4, and Grade 5, a grading system associated with the LOCS III grading system is available. Grade 1 is determined when the comparison of the volume of the first template 40 with the mean optical density of the lens is less than or equal to 13 percent. Grade 2 is determined when volume of template 40 with the mean optical density of the lens is between 14 and 16 percent. Grade 3 is determined when the comparison of the volume of the first template 40 with the mean optical density of the lens is between 17 percent and 19 percent. A table illustrating the grades compared to LOCS III grading is provided in FIG. 3. Though not illustrated, Grade 0 is determined when the comparison of the volume of the first template 40 with the mean optical density of the lens is 0 percent.

If the optical density of the lens determined by comparing the three-dimensional image with the first template exceeds a predefined value, such as but not limited to being greater than generally a 20 percent difference, then the cataract is either a Grade 4 or Grade 5, and a second template is applied, in a same manner as the first template 40, to determine the exact grade, at 18. The second template 42 is created, at 22, and is based on an optimal shape, optimal size, and/or optimal volume wherein the optimal shape, optimal size and/or optimal volume are larger than the optimal shape, optimal size and/or optimal volume of the first template 40. The dimensions of the second template are a diameter between 4.0 mm and 6.00 mm with a preferred measurement of 5.0 mm, a central thickness between 1.5 mm and 3.5 mm with a preferred measurement of 2.5 mm, and having the same measurements for the anterior radius of curvature and posterior radius of curvature. The volume of the second template is from 30 $mm^3$ to 34 $mm^3$ with a preferred measure of 30.97 $mm^3$.

With the second template in place, a mean optical density is determined when trying to determine if the cataract is Grade 4 or Grade 5. If the mean optical density is less than 20 percent with the second template, then the cataract is Grade 4. However, if the mean optical density is greater than 20 percent, then the cataract is Grade 5.

In another exemplary embodiment, a third template 44 is further used to determine whether the cataract is Grade 4 or Grade 5. The three-dimensional image of the lens is compared to the volume of the third template. The third template 44 has a volume larger than both the first template 40 and the second template 42, such as but not limited to 39.97 $mm^3$. Therefore if the second template 42 provides a predetermined value greater than 20 percent and the third template 44 also results provides for a predetermined value less than 20 percent, the cataract is a Grade 4. If each comparison of the volume of the third template 44 with the three-dimensional image of the lens provides for a predefined value being greater than or equal to 20 percent, the cataract is Grade 5.

Figure 4:
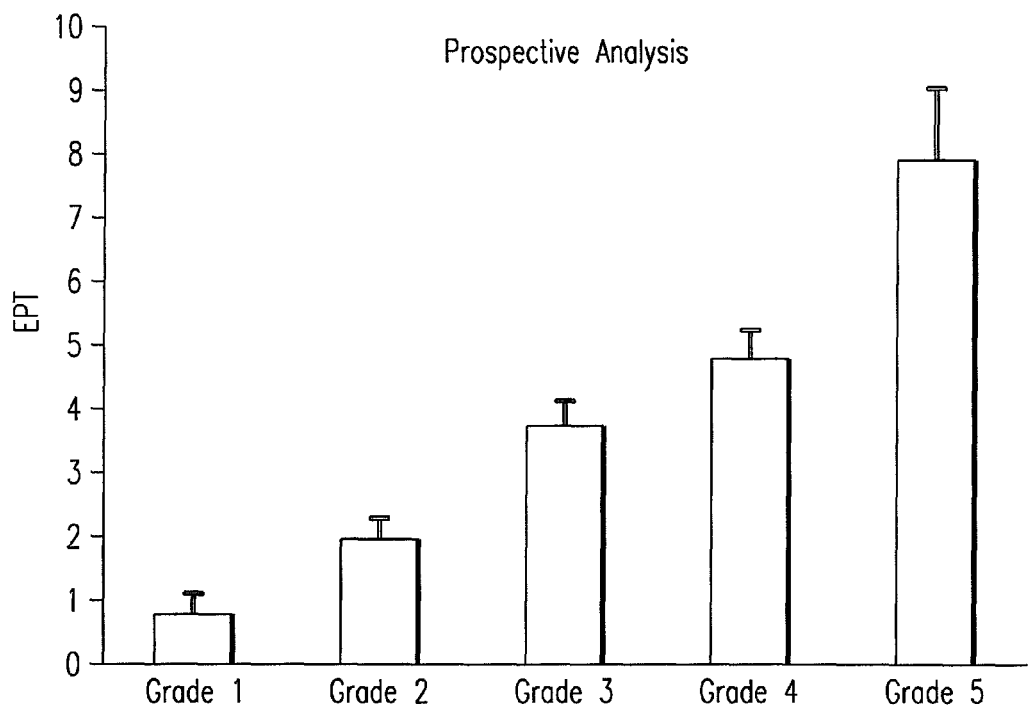
FIG. 4 is a graph illustrating an exemplary embodiment of equivalent phaco time (EPT) versus each grade level.

Based on the grade of the cataract, a linear relationship may be made as to an amount of energy required to remove the cataract of a particular grade Therefore, a relationship may be realized when determining an equivalent phacomulsification ("phaco") time (EPT) based on a grade determined for the cataract. The specific EPT setting, however is individual to a phaco system used to remove the cataract. EPT is calculated as a product of phaco power (or energy) and time duration. During phacoemulsification, or any other cataract surgery, knowing the ratio as it is associated with a particular phaco system, an improvement in phaco efficiency may be realized, where a reduction in an amount of energy and fluid dispersed in an eye may be possible. FIG. 4 depicts an exemplary relationship of EPT versus each grade. Based on the grading system disclosed herein, EPT standardization is possible between surgeons.

Figure 5:
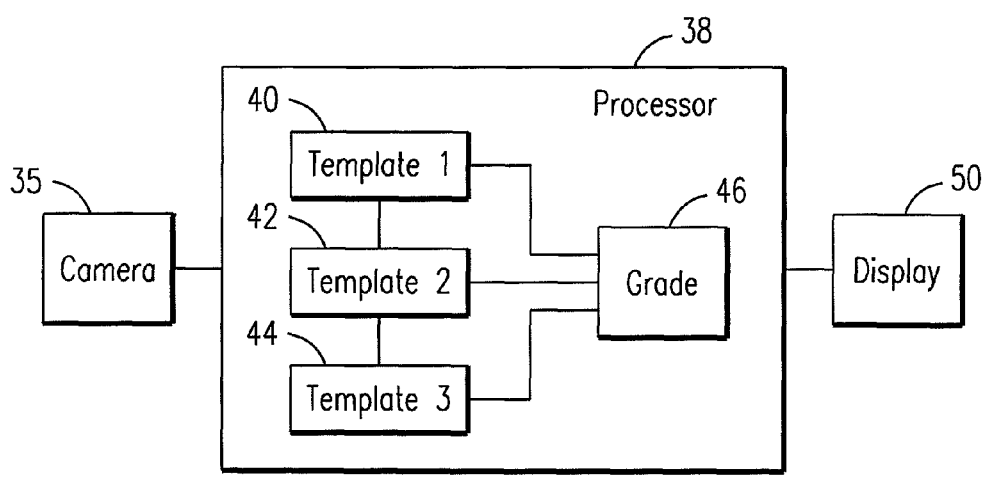
FIG. 5 is a block diagraph illustrating an exemplary embodiment of a system for grading a cataract.

FIG. 5 is a block diagraph illustrating an exemplary embodiment of a system for grading a cataract. An imaging system 35, or camera, that captures a three-dimensional image of lens having a cataract is used. As disclosed above, the imaging system 35 utilizes light reflection technology, such as, but not limited to including to the Scheimpflug principle. A first template 40 having a defined volume is also a part of the system. A processor 38 is also included. The processor 38 compares the three-dimensional image with a first template 40 to determine an optical density of the lens. The processor 38 further determines a grade for the cataract based on the comparison of the optical density of the lens and a volume of the first template 40. In an exemplary embodiment, the processor 38 is able to create the three-dimensional image from information provided by the imaging system 35.

A second template 42 is also disclosed. The second template 42 has a defined volume greater than the first template 40. As disclosed above, if the optical density of the lens determined by comparing the three-dimensional image with the first template exceeds a predefined value, such as but not limited to approximately twenty percent, the processor 38 compares the three-dimensional image to the second template 42, which has a greater volume than the first template 40, to determine the optical density of the lens. The processor further determines a grade for the cataract based on the comparison of the optical density of the lens and the volume of the second template 42.

Thus, as explained above, a first three grades for the cataract, or first group of grades, Grade 0, Grade 1, Grade 2, and Grade 3, are determinable with the first template 40. The second group of grades, Grade 4 and Grade 5, are determinable with the second template 42. As disclosed above, a third template 44 may be used to further distinguish between the grades in the second group of grades, Grade 4 and Grade 5.

A subsystem 46 within the processor 38 can determine grade of the cataract. A display device 50 is also disclosed. The display device 50 may be used to display the cataract grade determined. Though the term "display device" is used herein, the display device may comprise any form of communication that a user may receive, such as but not limited to audible and/or visible. Therefore, other than visually providing the cataract grade, the display device may, in conjunction with or without a visible rendition, provide an audible communication of the cataract grade determined.

The method illustrated in FIG. 1 may be performed with a computer software code having computer software modules, where the computer software code is stored on a computer media and is executed with a processor. Thus, each process flow in the flowchart 10 is performed by a computer software module specific to the process contained in the specific process.

While the invention has been described with reference to various exemplary embodiments, it will be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc., do not denote any order or importance, but rather the terms first, second, etc. are used to distinguish one element from another.

What is claimed is:

1. A method for grading a cataract, the method comprising:
creating a three-dimensional image of at least most of a lens of an eye having a cataract from information received from an imaging system;
comparing the three-dimensional image with a first three-dimensional template, configured to be a standard for use with a plurality of lenses, to determine an optical density of the lens; and
determining a grade for the cataract based on the comparison of the optical density of the lens and a volume of the first template.

2. The method according to claim 1, further comprises if the optical density of the lens determined by comparing the three-dimensional image with the first template exceeds a predefined value, comparing the three-dimensional image to a second three-dimensional template having a greater volume than the first template to determine the optical density of the lens, and determining a grade for the cataract based on the comparison of the optical density of the lens and the volume of the second template.

3. The method according to claim 1, wherein creating the three-dimensional image further comprises creating a three-dimensional image of an anterior segment of the eye that includes at least most of the lens having the cataract.

4. The method according to claim 1, further comprising creating the first template based on an optimal shape, optimal size, and/or optimal volume.

5. The method according to claim 2, further comprising creating the second template based on an optimal shape, optimal size, and/or optimal volume wherein the optimal shape, optimal size, and/or optimal volume of the second template is larger than the optimal shape, optimal size and/or optimal volume of the first template.

6. A system for grading a cataract, the system comprising:
an imaging system that captures a three-dimensional image of at least most of a lens of an eye having a cataract;
a first three-dimensional template having a defined volume; and
a processor that compares the three-dimensional image with a first template to determine an optical density of the lens, and determines a grade for the cataract based on the comparison of the optical density of the lens and a volume of the first template;
wherein the first template is configured to be a standard for use with a plurality of lenses.

7. The system according to claim 6, further comprising a second three-dimensional template having a defined volume greater than the first template, wherein if the optical density of the lens determined by comparing the three-dimensional image with the first template exceeds a predefined value, comparing the three-dimensional image to a second template having a greater volume than the first template to determine the optical density of the lens, and determining a grade for the cataract based on the comparison of the optical density of the lens and the volume of the second template.

8. The system according to claim 6, wherein an optimal shape, optimal size and/or optimal volume of the first template comprises an average diameter of 3.0 mm to 5.0 mm, an average depth of 1.0 mm to 3.0 mm, an average anterior radius of curvature of 4.0 mm to 6.0 mm, an average posterior radius of curvature of 3.0 mm to 5.0 mm, and/or an average volume of 20.0 $mm^3$ to 21.5 $mm^3$.

9. The system according to claim 7, an optimal shape, optimal size and/or optimal volume of the second template comprises an average diameter of 4.0 mm to 6.0 mm, an average depth of 1.5 mm to 3.5 mm, and average depth of 1.0 mm to 3.0 mm, an average radius of curvature of 4.0 mm to 6.0 mm, an average posterior radius of curvature of 3.0 mm to 5.0 mm, and/or an average volume of 30 $mm^3$ to 34 $mm^3$.

10. The system according to claim 6, wherein the imaging system utilizes the Scheimpflug principle to capture an image.

11. The system according to claim 6, wherein a first group of grades, Grade 0, Grade 1, Grade 2, and Grade 3, are determinable with the first template.

12. The system according to claim 7, wherein a second group of grades, Grade 4 and Grade 5 are determinable with the second template.

13. The system according to claim 7, wherein the second template is used when the predefined value is greater than approximately twenty percent.

14. The system according to claim 6, further comprises a display device to inform a user of a grade for the cataract.

15. A computer software code stored on a computer readable medium and configured for execution with a processor for grading a cataract, the computer software code comprising:
a computer software module for creating a three-dimensional image of at least most of a lens of an eye having a cataract from information received from an imaging system;
a computer software module for comparing the three-dimensional image with a first three-dimensional template, configured to be a standard for use with a plurality of lenses, to determine an optical density of the lens; and
a computer software module for determining a grade for the cataract based on the comparison of the optical density of the lens and a volume of the first template.

16. The computer software code according to claim 15, further comprises if the optical density of the lens determined by comparing the three-dimensional image with the first template exceeds a predefined value, a computer software module for comparing the three-dimensional image to a second three-dimensional template having a greater volume than the first template to determine the optical density of the lens, and determining a grade for the cataract based on the comparison of the optical density of the lens and the volume of the second template.

17. The system according to claim 1, wherein the first three-dimensional template is a hybrid of a combination of a sphere and a cube.

18. The system according to claim 6, wherein the first three-dimensional template is a hybrid of a combination of a sphere and a cube.

19. The system according to claim 15, wherein the first three-dimensional template is a hybrid of a combination of a sphere and a cube.

* * * * *